US012404225B2

United States Patent
Schulz et al.

(10) Patent No.: US 12,404,225 B2
(45) Date of Patent: Sep. 2, 2025

(54) METHOD AND SYSTEM FOR THE SYNTHESIS OF METHANOL

(71) Applicants: thyssenkrupp Industrial Solutions AG, Essen (DE); thyssenkrupp AG, Essen (DE)

(72) Inventors: Alexander Schulz, Frankfurt (DE); Nicolas Von Winning, Bad Homburg vor der Höhe (DE); Sina Kunz, Frankfurt (DE)

(73) Assignees: thyssenkrupp Uhde GmbH, Dortmund (DE); thyssenkrupp AG, Essen (DE)

( * ) Notice: Subject to any disclaimer, the term of this patent is extended or adjusted under 35 U.S.C. 154(b) by 656 days.

(21) Appl. No.: 17/611,320

(22) PCT Filed: May 6, 2020

(86) PCT No.: PCT/EP2020/062572
§ 371 (c)(1),
(2) Date: Nov. 15, 2021

(87) PCT Pub. No.: WO2020/229261
PCT Pub. Date: Nov. 19, 2020

(65) Prior Publication Data
US 2022/0162143 A1    May 26, 2022

(30) Foreign Application Priority Data

May 16, 2019 (DE) ............ 10 2019 113 003.4

(51) Int. Cl.
*C07C 29/152* (2006.01)
*B01D 53/047* (2006.01)
*B01D 53/22* (2006.01)
*B01J 19/24* (2006.01)

(52) U.S. Cl.
CPC .......... *C07C 29/152* (2013.01); *B01D 53/047* (2013.01); *B01D 53/229* (2013.01); *B01J 19/245* (2013.01); *B01J 19/2465* (2013.01); *B01D 2256/16* (2013.01); *B01D 2257/504* (2013.01)

(58) Field of Classification Search
USPC ........................................... 568/884
See application file for complete search history.

(56) References Cited

U.S. PATENT DOCUMENTS

| 4,181,675 A  * | 1/1980  | Makin ............... C07C 29/1512 |
| | | 95/55 |
| 5,827,901 A  | 10/1998 | Konig et al. |
| 10,364,202 B2 * | 7/2019 | Kopetsch .............. C07C 29/152 |
| 2007/0282020 A1 | 12/2007 | Fraley |
| 2009/0018220 A1 * | 1/2009 | Fitzpatrick ............. C12C 11/02 |
| | | 518/700 |
| 2019/0047931 A1 * | 2/2019 | Balthasar ................ C01B 3/382 |

FOREIGN PATENT DOCUMENTS

| CN | 109071387 A | 12/2018 |
| DE | 10 2019 203 065 A1 | 9/2020 |
| EP | 3219697 A1 | 9/2017 |
| JP | 2009-179591 A | 8/2009 |
| WO | 2014/173452 A1 | 10/2014 |
| WO | WO-2018019875 A1 * | 2/2018 ............... C07C 1/12 |

OTHER PUBLICATIONS

English Translation of International Search Report issued in PCT/EP2020/062572, dated Jul. 13, 2020.

* cited by examiner

*Primary Examiner* — Ana Z Muresan
(74) *Attorney, Agent, or Firm* — thyssenkrupp North America, LLC (57) ABSTRACT

A process for synthesizing methanol may involve supplying a CO2 stream consisting predominantly of carbon dioxide and an H stream consisting predominantly of hydrogen to a methanol reactor arrangement for conversion to methanol. A tail gas stream comprising unreacted hydrogen may be obtained from the methanol reactor arrangement. The unreacted hydrogen may be at least partly recycled to the methanol reactor arrangement. The tail gas stream is supplied to a hydrogen recovery arrangement to obtain a return stream comprising the unreacted hydrogen. The molar proportion of hydrogen in the return stream may be higher than in the tail gas stream.

18 Claims, 6 Drawing Sheets

METHOD AND SYSTEM FOR THE SYNTHESIS OF METHANOL

CROSS REFERENCE TO RELATED APPLICATIONS

This application is a U.S. National Stage Entry of International Patent Application Serial Number PCT/EP2020/062572, filed May 6, 2020, which claims priority to German Patent Application No. DE 10 2019 113 003.4, filed May 16, 2019, the entire contents of both of which are incorporated herein by reference.

FIELD

The present disclosure generally relates to the synthesis of methanol, including methods and systems for the synthesis of methanol.

BACKGROUND

Methanol is prepared by an exothermic reaction that uses hydrogen and carbon oxides as reactants, which are supplied as a gas stream to an appropriate reactor for methanol synthesis. These substances may be obtained from various sources.

A first option is to subject a carbonaceous energy carrier stream to steam reforming or, for instance, to a catalytic partial oxidation, so as to obtain a synthesis gas comprising essentially hydrogen and carbon oxides. According to the type of energy carrier and mode of production of the synthesis gas, different proportions of hydrogen and the carbon oxides—and hence a different stoichiometry—are achieved in the synthesis gas. The resulting stoichiometry can then be adjusted by various measures, for instance by subjecting it to a water-gas shift reaction. One advantage of this approach is that the energy carrier itself—for instance natural gas—can regularly be provided at a high pressure, such that only a comparatively small increase in pressure is necessary after the synthesis gas has been obtained for attainment of the pressure required for the methanol synthesis.

A further option for providing the reactants for the synthesis of methanol is to use a gas stream having a high carbon dioxide content and without hydrogen. Such a gas stream can be obtained, for instance, from a flue gas, i.e. from an offgas from a combustion. It would likewise be possible to obtain such a gas stream from a plant for preparation of bioethanol. Since such a flue gas thus does not include any hydrogen, it is necessary in this variant to provide hydrogen from another source, for example from an electrolysis.

Regularly, for the methanol synthesis, the gas comprising the reactants is circulated in a circuit, since a single pass of this gas through the reactor typically does not lead to sufficiently substantial conversion to methanol. The methanol converted is regularly removed from the circulating gas by condensation. At the same time, however, the circulation also results in accumulation of inert substances that cannot be sufficiently removed by this condensation. For removal of these substances from the circuit, it is necessary to remove a portion of the circulating gas as purge gas, which purge gas can then be burned, for example.

WO 2014/173452 A1, which is the closest to the present invention, describes such a process and a corresponding plant for the synthesis of methanol from a carbon dioxide stream and a separate hydrogen stream.

WO 2018/019875 A1 likewise discloses such a process and a corresponding plant.

A disadvantage of this prior art is that hydrogen is always also removed when gas is discharged. This discharged hydrogen is thus lost to the methanol synthesis.

SUMMARY

Thus a need exists to reduce the proportion of hydrogen in the purge gas and hence to minimize the loss of hydrogen, which is relatively valuable for methanol synthesis.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The invention is based on the finding that hydrogen can be recovered from a tail gas from a methanol reactor prior to removal thereof, and the hydrogen recovered can then be returned to the methanol synthesis. In this way, the hydrogen can be utilized for the methanol synthesis and is not just burnt.

The process proposed serves for synthesis of methanol, wherein a CO2 stream consisting predominantly of carbon dioxide and an H stream consisting predominantly of hydrogen are supplied to a methanol reactor arrangement for conversion to methanol. What is meant by the CO2 stream consisting predominantly of carbon dioxide is that the molar proportion of carbon dioxide of the CO2 stream is at least 50%. The molar proportion of carbon dioxide in the CO2 stream is preferably at least 95% and especially at least 99%. What is meant by the H stream consisting predominantly of hydrogen is correspondingly that the molar proportion of hydrogen in the H stream is at least 50%. The molar proportion of hydrogen in the H stream is preferably at least 95% and especially at least 99%. The conversion of the substances supplied to methanol is regularly incomplete.

In the process proposed, a tail gas stream comprising unreacted hydrogen is obtained from the methanol reactor arrangement, and the unreacted hydrogen is returned at least partly to the methanol reactor arrangement. The tail gas stream may, as well as the unreacted hydrogen, also include unreacted carbon dioxide, and also carbon monoxide formed in the methanol reactor arrangement, especially by the reverse water-gas shift reaction. The tail gas stream for the methanol synthesis may likewise include inert constituents such as nitrogen, methane and noble gases, and also by-products such as dimethyl ether. It is preferable that the methanol reactor arrangement is encompassed by a plant for synthesis of methanol.

The process proposed is characterized in that the tail gas stream is supplied to a hydrogen recovery arrangement to obtain a return stream comprising the unreacted hydrogen. The process proposed is further characterized in that the return stream consists predominantly of hydrogen. This means that the molar proportion of hydrogen in the return stream is at least 50%. The molar proportion of hydrogen in the return stream is preferably at least 95% and especially at least 99%. It is likewise preferable that the molar hydrogen content in the return stream is higher than in the tail gas stream. The hydrogen recovery arrangement results in enrichment of hydrogen. The plant for synthesis of methanol preferably comprises the hydrogen recovery arrangement.

It is preferable that a purge stream is also obtained from the hydrogen recovery arrangement, which purge stream preferably has a smaller molar proportion of hydrogen than the tail gas stream. In this way, a greater proportion of hydrogen is returned than is removed via the purge stream. In principle, the purge stream may be removed to any further use. For instance, the purge stream may be routed to a flare or to a catalytic postcombustion.

It is preferable that the purge stream is fed as fuel to a firing apparatus of a chemical plant for obtaining a substance. The substance obtained is a substance other than methanol. This chemical plant is preferably an additional plant with respect to the plant for synthesis of methanol. But this chemical plant may have apparatuses in common with the proposed plant for synthesis of methanol, especially the hydrogen recovery arrangement. This chemical plant is likewise preferably a plant for obtaining a substance from a hydrocarbonaceous starting stream. Alternatively or additionally, the chemical plant is set up to recover a hydrocarbonaceous product stream. The energy from the firing apparatus in the chemical plant can be used for basically any purpose. It is preferable that the energy from the firing apparatus is used in the chemical plant for heating of a process stream and/or for raising steam. The chemical plant may especially be a steamcracker, a hydrogen plant or a dehydrogenation plant.

A preferred embodiment of the process proposed is characterized in that the return stream is supplied as H stream to the methanol reactor arrangement. In this way, the return stream can predominantly or even completely provide the hydrogen for the methanol synthesis. This is possible especially when the hydrogen recovery arrangement is supplied not just with the tail gas stream but also with one or more further hydrogen-containing streams. The return stream may then include the hydrogen from all these hydrogen-containing streams. It may be the case here that the hydrogen recovery arrangement is encompassed by the chemical plant. In such a case, it is thus possible to branch off a regularly relatively small proportion of hydrogen from the hydrogen recovery arrangement in the chemical plant, which does of course serve a different purpose than the synthesis of methanol, for the synthesis of methanol.

It may especially be the case that a hydrogen-containing fresh gas stream is fed to the hydrogen recovery arrangement to obtain the return stream. The hydrogen-containing fresh gas stream may especially be obtained from a hydrogen-obtaining arrangement, i.e. a plant for obtaining a hydrogen stream. The hydrogen-obtaining arrangement may be encompassed by the chemical plant. In this way, double utilization also takes place for the recovery of hydrogen.

But it may also be the case that, in addition to the hydrogen from the return stream, a fresh gas stream of hydrogen is supplied to the methanol reactor arrangement. A corresponding further preferred embodiment of the process proposed is characterized in that the H stream is a fresh gas stream from a hydrogen-obtaining arrangement, and in that the return stream is returned additionally to the H stream to the methanol reactor arrangement for conversion to methanol. This approach reduces the demands on the processing capacity of the hydrogen recovery arrangement. The hydrogen-obtaining arrangement may comprise a plant for obtaining hydrogen by electrolysis. The plant for synthesis of methanol preferably comprises the hydrogen-obtaining arrangement. Alternatively, the chemical plant may comprise the hydrogen-obtaining arrangement.

In principle, the hydrogen recovery arrangement can perform the hydrogen recovery in accordance with any technical principle. In a preferred embodiment of the process proposed, the hydrogen recovery arrangement includes a pressure swing adsorption (PSA) apparatus. It may especially be the case that the hydrogen recovery arrangement includes a pressure swing adsorption apparatus for obtaining the return stream from the tail gas stream. The pressure swing adsorption apparatus may likewise be set up to obtain the purge stream. Such a pressure swing adsorption apparatus achieves a very high purity in the return stream and is associated with a comparatively small pressure drop, such that the return stream has to be repressurized only to a small degree for the methanol synthesis. In a further preferred embodiment of the process proposed, the hydrogen recovery arrangement includes a further pressure swing adsorption (PSA) apparatus, and the further pressure swing adsorption apparatus is connected downstream of the pressure swing adsorption apparatus in the processing operation. In this case, an output stream from the pressure swing adsorption apparatus of the further pressure swing adsorption apparatus may be set up to obtain a further return stream comprising hydrogen from the output stream, in which case the further return stream is sent to the methanol reactor arrangement for conversion to methanol.

In a further preferred embodiment of the process proposed, the hydrogen recovery arrangement includes a membrane apparatus. It may especially be the case that the hydrogen recovery arrangement includes a membrane apparatus for obtaining the return stream from the tail gas stream. The membrane apparatus is preferably set up to separate off hydrogen.

Alternatively, it is possible to combine various modes of hydrogen recovery in the hydrogen recovery arrangement. For instance, in a preferred variant, the tail gas stream is fed to the membrane apparatus to obtain a membrane hydrogen stream and a membrane tail stream, and the membrane tail stream is fed to the pressure swing adsorption apparatus to obtain a PSA hydrogen stream. In such a case, either the membrane hydrogen stream or the PSA hydrogen stream may form the return stream and the respective other stream the further return stream, in which case the further return stream is fed to the methanol reactor arrangement for conversion to methanol. It is also possible to feed both return streams to the methanol reactor arrangement for conversion to methanol. It is alternatively possible to combine the membrane hydrogen stream and the PSA hydrogen stream to give the return stream.

In a further preferred embodiment of the process proposed, the membrane hydrogen stream is obtained from a low-pressure side of the membrane apparatus, and the membrane tail stream is obtained from a high-pressure side of the membrane apparatus. It may thus be the case that the membrane hydrogen stream is obtained at a lower pressure than the membrane tail stream.

As well as the return stream, it is also possible to return further streams to the methanol reactor arrangement. A preferred embodiment of the process proposed is characterized in that a recycle stream comprising further unreacted tail gas of the methanol reactor arrangement is returned to the methanol reactor arrangement for partial conversion to methanol. This is unreacted tail gas in addition to the unreacted tail gas from the tail gas stream. It is preferable here that the recycle stream is pressurized by a recycle compressor arrangement before being returned to the methanol reactor arrangement. In this way, recirculation of the carbon dioxide and of any carbon monoxide formed in the methanol reactor arrangement also takes place. The plant for synthesis of methanol preferably encompasses the recycle compressor arrangement.

The recycle compressor arrangement may also be used to pressurize the return stream. A further preferred embodiment of the process proposed is therefore characterized in that the return stream is fed into the recycle stream. More particularly, the return stream may be fed into the recycle stream prior to pressurization by the recycle compressor arrangement.

In a preferred embodiment of the process proposed, the methanol reactor arrangement comprises a methanol separation arrangement for obtaining the tail gas stream and a crude methanol stream. It is likewise preferable that the recycle stream is obtained from the methanol separation arrangement. The tail gas stream may be obtained from the methanol separation arrangement in that the tail gas stream is branched off from the recycle stream.

In a preferred embodiment of the process proposed, the crude methanol stream is sent to a distillation to obtain the methanol. The plant for synthesis of methanol preferably encompasses the distillation.

It may be the case in principle that the methanol reactor arrangement comprises just a single reactor stage or else just a single reactor for the methanol synthesis. Within a single reactor stage, it is possible to connect multiple reactors for the methanol synthesis in parallel in the processing operation. In a further preferred embodiment of the process proposed, the methanol reactor arrangement has a multitude of reactor stages for methanol synthesis that are connected in series in the processing operation. It is not necessary here for the reactor stages to follow on directly from one another in the processing operation.

In accordance with the multitude of reactor stages, it is also possible for the methanol separation arrangement to be in multistage form. For instance, it is preferable that the methanol separation arrangement comprises a multitude of methanol separation apparatuses, wherein each methanol separation apparatus of the multitude of methanol separation apparatuses is connected downstream in the processing operation of a reactor stage of the multitude of reactor stages. In other words, each methanol separation apparatus is connected downstream in the processing operation of a single one of the reactor stages and, if the reactor stage is not the last in the processing operation, upstream of the next reactor stage. By removing methanol and water after each individual reactor stage, it is possible to improve the reaction equilibrium for each downstream reactor stage.

A preferred embodiment of the process proposed is characterized in that a crude methanol substream and a stage tail gas stream comprising unreacted hydrogen are obtained from each of the methanol separation apparatuses of the multitude of methanol separation apparatuses. The stage tail gas stream may also include carbon monoxide, nitrogen, methane, noble gases and/or further constituents. The stage tail gas stream may likewise also include unreacted carbon dioxide. It may especially be the case that, up to a last reactor stage in the series of the multitude of reactor stages, each stage tail gas stream from one of the methanol separation apparatuses is fed to a downstream reactor stage in the processing operation. In other words, the removal of methanol takes place at first after each reaction stage, and the remaining tail gas is supplied to the respective next reactor stage if there is such a next reactor stage. It is further preferable that the crude methanol substreams are combined to give the crude methanol stream.

In principle, the reactor stages may have reactors of any type. A further preferred embodiment of the process proposed is characterized in that at least one of the reactor stages for methanol synthesis includes an isothermal reactor or consists of an isothermal reactor. It may especially be the case that all reactor stages for methanol synthesis each have an isothermal reactor or each consist of an isothermal reactor.

In a further preferred embodiment of the process proposed, the CO2 stream and the H stream, and preferably also the return stream, are fed to a first reactor stage of the multitude of reactor stages. It is likewise preferable that the pressurized recycle stream is fed to the first reactor stage.

A preferred embodiment of the process proposed is characterized in that the tail gas stream is obtained from a methanol separation apparatus which is connected downstream of a tail gas recovery reactor stage in the processing operation, wherein the tail gas recovery reactor stage is connected downstream of the first reactor stage in the processing operation. In other words, it is the case here that the tail gas stream is obtained after a particular reactor stage, which is referred to here as the tail gas recovery reactor stage. This tail gas recovery reactor stage is connected downstream of the first reactor stage, i.e. is a stage other than the first reactor stage. Specifically, the tail gas stream is obtained from that methanol separation apparatus which specifically follows this tail gas recovery reactor stage in the processing operation. The tail gas recovery reactor stage is preferably the last in the series in the processing operation among the multitude of reactor stages. In other words, the last reactor stage is the tail gas recovery reactor stage.

A further preferred embodiment of the process proposed is characterized in that the CO2 stream and the H stream, and preferably also the return stream, before being fed to the methanol reactor arrangement, are pressurized by a feed gas compressor arrangement. In principle, the feed gas compressor arrangement may be in one-stage form, such that the feed gas compressor arrangement has only a single compressor stage. Preferably, the CO2 stream and the H stream, and preferably also the return stream, are pressurized by the feed gas compressor arrangement to a synthesis pressure between 50 bar and 80 bar.

It is preferable that the feed gas compressor arrangement has a multitude of compressor stages for pressurization that are connected in series in the processing operation. The feed gas compressor arrangement preferably has four compressor stages. Such a multistage configuration means makes it possible for particular streams that can be provided at a higher pressure not to have to pass through all compressor stages. The multitude of compressor stages may be a multitude of compressor stages of a single compressor, such that the multitude of compressor stages has a common shaft. It is likewise alternatively possible for the multitude of compressor stages to be formed by a multitude of single compressors.

It is thus especially preferable that the H stream is supplied to the feed gas compressor arrangement for pressurization between different compressor stages of the multitude of compressor stages than the CO2 stream. This is an option when the H stream is provided at a different pressure than the CO2 stream. It is alternatively possible that the H stream is supplied between those compressor stages of the multitude of compressor stages for pressurization between which the CO2 stream is also supplied. This is advantageous when the H stream is provided at the same pressure as the CO2 stream. It may likewise be the case that the return stream is supplied between different compressor stages of the multitude of compressor stages of the feed gas compressor arrangement for pressurization than the further return stream. The plant for synthesis of methanol preferably encompasses the feed gas compressor arrangement.

In a preferred embodiment of the process proposed, the CO2 stream consists essentially of carbon dioxide. It may alternatively or additionally be the case that the H stream consists essentially of hydrogen.

The plant proposed serves for synthesis of methanol and has a methanol reactor arrangement which is supplied with a CO2 stream consisting predominantly of carbon dioxide and an H stream consisting predominantly of hydrogen for partial conversion to methanol.

In the plant proposed, a tail gas stream comprising unreacted hydrogen is obtained from the methanol reactor arrangement, and the unreacted hydrogen in the tail gas stream is at least partly returned to the methanol reactor arrangement.

The plant proposed is characterized in that the plant has a hydrogen recovery arrangement which is supplied with the tail gas stream for obtaining a return stream comprising the unreacted hydrogen, and in that the molar hydrogen content in the return stream is higher than in the tail gas stream.

Features, advantages and properties of the plant proposed correspond to the features, advantages and properties of the process proposed, and vice versa.

Figure 1:
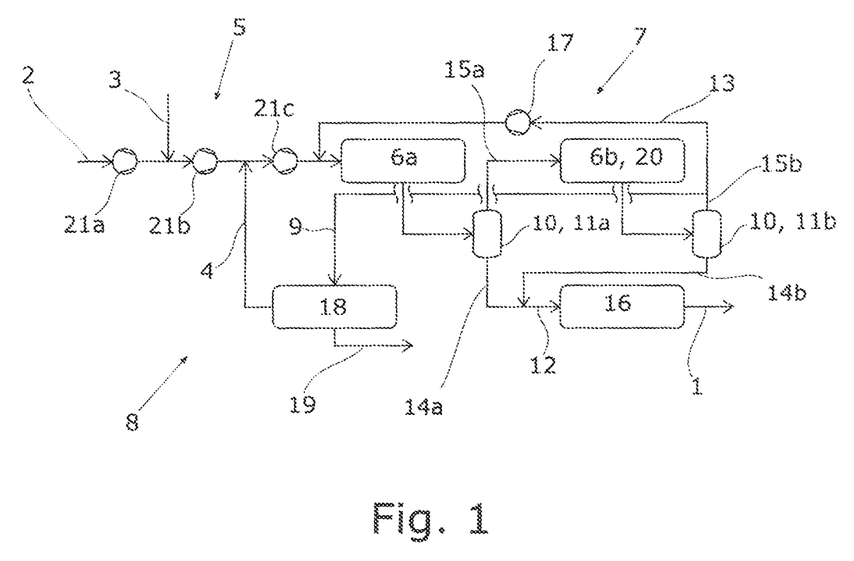
FIG. 1 is a schematic flow diagram of an example plant for executing the process of a first working example.

The plant according to a first working example of the plant proposed as shown in FIG. 1 serves for synthesis of methanol 1 and can be operated by the process proposed.

A CO2 stream 2 consisting essentially of carbon dioxide, an H stream 3 consisting essentially of hydrogen, and a return stream 4 likewise consisting essentially of hydrogen are pressurized by a feed gas compressor arrangement 5 and then fed to a first reactor stage 6a of a methanol reactor arrangement 7.

This feed gas compressor arrangement 5 is in multistage form. By way of simplification, the feed gas compressor arrangement 5 here is represented by three compressor stages 21a-c of a single compressor that are series-connected in the processing operation, where a feed gas compressor arrangement 5 may regularly have four compressor stages. It is apparent that the CO2 stream 2, the H stream 3 and the return stream 4 are each supplied upstream of a different compressor stage 21a-c. The CO2 stream 2 is fed in at ambient pressure, and therefore is to be pressurized by all compressor stages 21a-c of the feed gas compressor arrangement 5 for attainment of the target pressure for the methanol synthesis, and it is consequently supplied directly to the first compressor stage 21a. The H stream 3 is fed in at a somewhat higher pressure and is therefore fed in downstream of the first compressor stage 21a and upstream of the second compressor stage 21b in the processing operation. Finally, the return stream 4 is fed in at the highest pressure, and therefore between the second compressor stage 21b and the third compressor stage 21c in the processing operation.

Likewise fed into the first reactor stage 6a is a recycle stream 13. In this first reactor stage 6a consisting of a single isothermal reactor, partial conversion of the carbon dioxide and of the hydrogen to methanol takes place.

The CO2 stream 2 is obtained from the flue gas from a power plant (not shown here). The H stream 3 is obtained from an electrolysis plant for obtaining hydrogen (likewise not shown here), wherein the H stream 3 in this example could also be obtained at ambient pressure. It is alternatively conceivable that the H stream 3 is provided at a lower pressure than the CO2 stream 2, in which case the feed to the the compressor stages 21a-c would be switched. The return stream 4 is obtained from a hydrogen recovery arrangement 8 of the plant, which is supplied for this purpose with a tail gas stream 9 from the methanol reactor arrangement 7, which includes unreacted reactants from the methanol synthesis and therefore unreacted hydrogen in particular.

Connected downstream of the first reactor stage 6a in the processing operation, albeit not directly, is a second reactor stage 6b of the methanol reactor arrangement 7, which second reactor stage 6b here likewise consists of a single isothermal reactor. The methanol reactor arrangement 7 has a methanol separation arrangement 10 which, through condensation of crude methanol, is set up to obtain the tail gas stream 9 and a crude methanol stream 12. The methanol separation arrangement 10 in turn consists here of a first methanol separation apparatus 11a connected between the first reactor stage 6a and the second reactor stage 6b in the processing operation, and a second methanol separation apparatus 11b connected downstream of the second reactor stage 6b in the processing operation.

The gas mixture comprising methanol and unreacted tail gas from the first reactor stage 6a is fed to the first methanol separation apparatus 11a, and a first crude methanol substream 14a, consisting essentially of crude methanol, and a first stage tail gas stream 15a comprising the unreacted tail gases from the first reactor stage 6a are obtained from this methanol separation apparatus 11a. The first stage tail gas stream 15a is fed to the second reactor stage 6b for methanol synthesis. Correspondingly, the gas mixture from the second reactor stage 6b is fed to the second methanol separation apparatus 11b, and a second crude methanol substream 14b and a second stage tail gas stream 15b are obtained therefrom. The first crude methanol substream 14a and the second crude methanol substream 14b are combined to give the crude methanol stream 12, which is in turn fed to a distillation 16 to obtain the methanol 1.

The second stage tail gas stream 15b is divided into the tail gas stream 9, which is of course fed to the hydrogen recovery arrangement 8, and the recycle stream 13. In this way, both the tail gas stream 9 and the recycle stream 13 are obtained from the methanol separation arrangement 10. The recycle stream 13 is fed to a recycle compressor arrangement 17 for increasing the pressure and then to the first reactor stage 6*a*. Since the tail gas stream 9 from the second reactor stage 6*b* is thus obtained directly downstream here, the second reactor stage 6*b* can be referred to as tail gas-obtaining reactor stage 20.

In the working example of FIG. 1, the hydrogen recovery arrangement 8 is a pressure swing adsorption apparatus 18 that affords the return stream 4 from the tail gas stream 9. Likewise obtained is a purge stream 19, which is fed to a firing apparatus (not shown here) of a separate chemical plant, where it is incinerated. The composition of the purge stream 19 corresponds essentially to the composition of the tail gas stream 9 minus the return stream 4. The hydrogen fed back to the methanol reactor arrangement 7 via the return stream 4 is not fired with the purge stream 19 but is available for the methanol synthesis.

Figure 2:
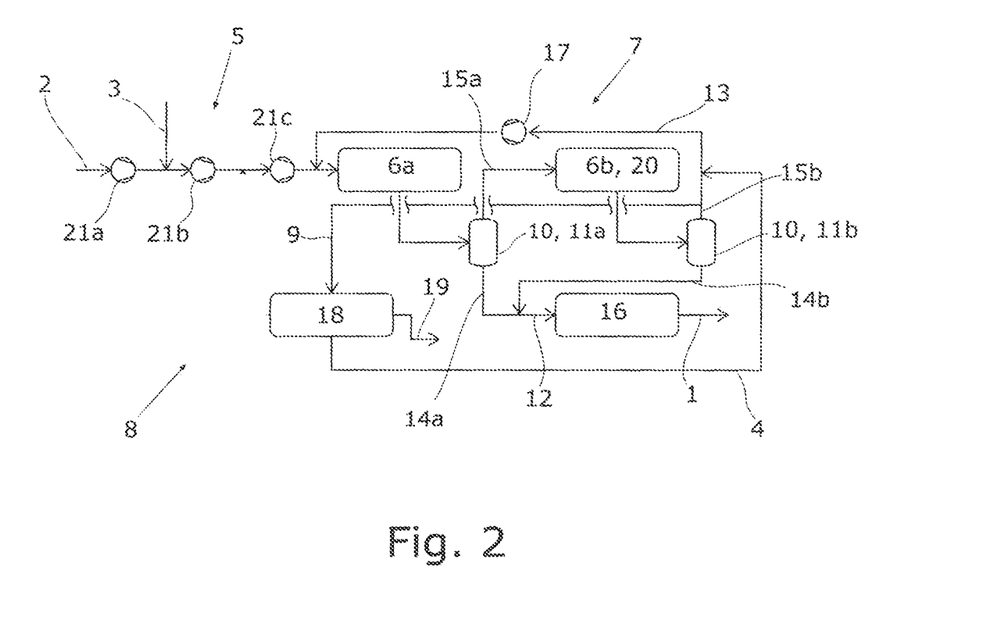
FIG. 2 is a schematic flow diagram of an example plant for executing the process of a second working example.

The plant according to a second working example of the plant proposed as shown in FIG. 2 may be operated by the process proposed. This working example corresponds in principle to the first working example of FIG. 1, except that the return stream 4 from the hydrogen recovery arrangement 8 is not pressurized by the feed gas compressor arrangement 5 before being fed to the first reactor stage 6*a*. Instead, the return stream 4 is fed into the recycle stream 13. This feed is effected upstream of the recycle compressor arrangement 17 in the processing operation, such that the return stream 4 is pressurized by the recycle compressor arrangement 17 together with the recycle stream 13. Compared to the working example of FIG. 1, this firstly reduces the burden on the feed gas compressor arrangement 5. It may likewise be the case that the pressure of the return stream 4 is close to the pressure of the recycle stream 13, such that the latter has to be expanded only slightly, and therefore combination of the return stream 4 with the recycle stream 13 is more favorable than supply of the return stream to the feed gas compressor arrangement 5.

Figure 3:
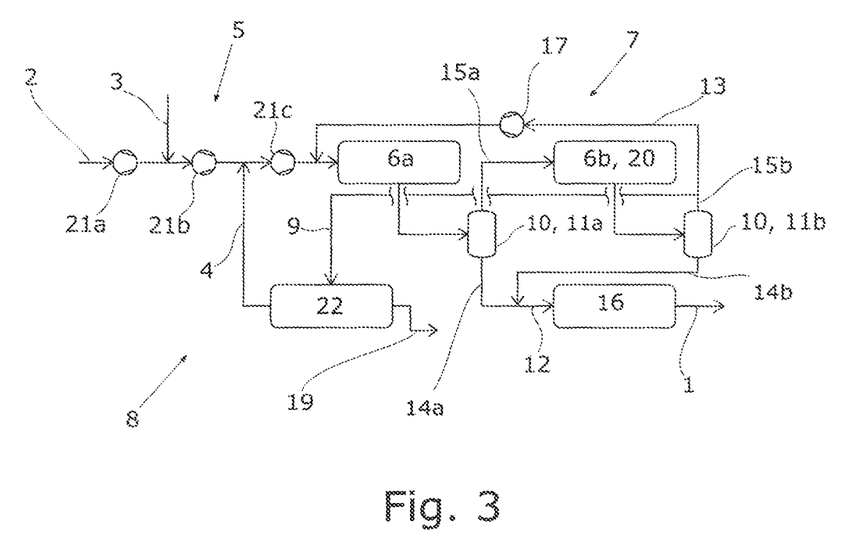
FIG. 3 is a schematic flow diagram of an example plant for executing the process of a third working example.

The plant according to a third working example of the plant proposed as shown in FIG. 3 may be operated by the process proposed. This working example likewise corresponds in principle to the first working example of FIG. 1, except that the hydrogen recovery arrangement 8 here consists of a membrane apparatus 22 for obtaining the return stream 4 and the purge stream 19. Especially when a relatively large pressure drop of the return stream 4 compared to the tail gas stream 9 is accepted—which can in principle be compensated for by the increase in pressure in the feed gas compressor arrangement 5—it is possible to recover a particularly high proportion of the hydrogen in the tail gas stream 9 via the return stream 4. Correspondingly, the loss of hydrogen in the purge stream 19 is low.

Figure 4:
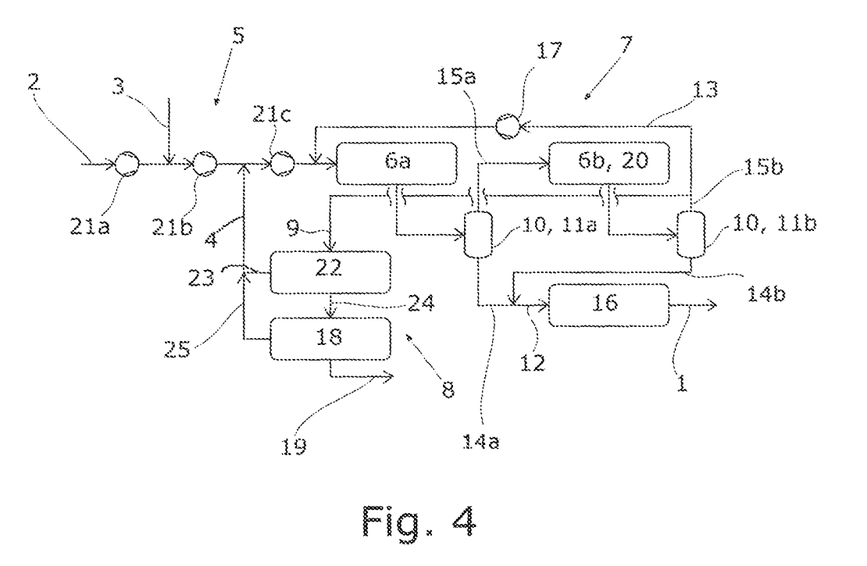
FIG. 4 is a schematic flow diagram of an example plant for executing the process of a fourth working example.

The plant according to a fourth working example of the plant proposed as shown in FIG. 4 proceeds from the third working example of FIG. 3 and can likewise be operated by the process proposed. Here, the hydrogen recovery apparatus 8 comprises both a membrane apparatus 22 and a pressure swing adsorption apparatus 18. Specifically, the tail gas stream 9 is fed to the membrane apparatus 22. A hydrogen-enriched membrane hydrogen stream 23 and a correspondingly low-hydrogen membrane tail stream 24 are obtained from the membrane apparatus 22. The membrane tail stream 24 is fed to the pressure swing adsorption apparatus 18, such that a PSA hydrogen stream 25 consisting essentially of hydrogen and the purge stream 19 are obtained therefrom in turn. The PSA hydrogen stream 25 is combined here with the membrane hydrogen stream 23 to give the return stream 4. But it would also be possible to guide only the membrane hydrogen stream 23 as return stream 4 and the PSA hydrogen stream 25 separately as further return stream to the feed gas compressor arrangement 5. In this case, it would be possible to feed in the membrane hydrogen stream 23 and the PSA hydrogen stream 25 upstream of different compressor stages 21*a-c* owing to their different pressure. Because the membrane apparatus 22 is connected upstream of the pressure swing adsorption apparatus 18 in the manner described for the fourth working example, the burden on the pressure swing adsorption apparatus 18 is reduced to such an extent that can have a smaller design. It is thus possible to return a very high proportion of the hydrogen in the tail gas stream 9 overall.

Figure 5:
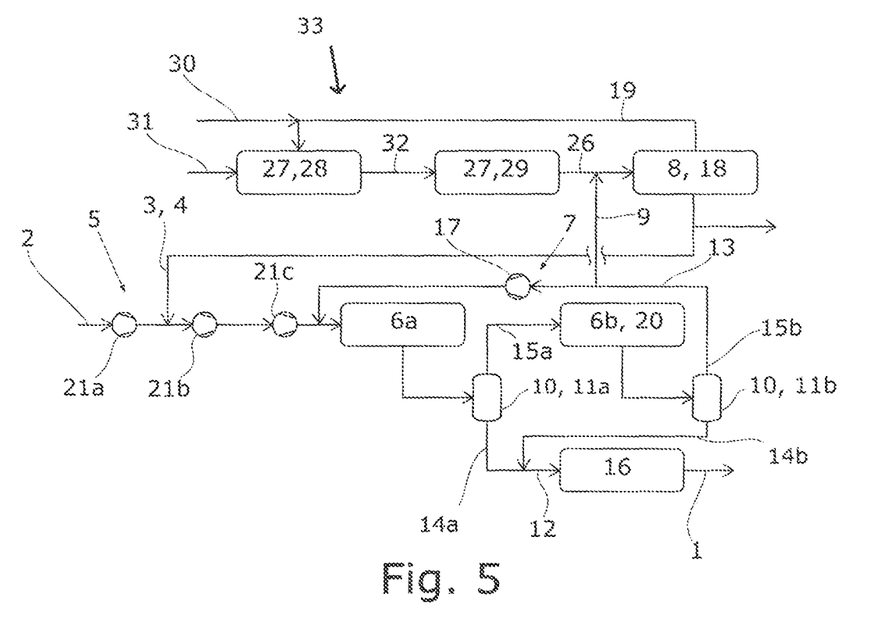
FIG. 5 is a schematic flow diagram of an example plant for executing the process of a fifth working example.

The plant according to a fifth working example of the plant proposed as shown in FIG. 5 may be operated by the method proposed and proceeds in principle from the first working example of FIG. 1, except that—as will be described in detail—the H stream 3 is not obtained from an electrolysis. However, the hydrogen recovery arrangement 8 designed as a pressure swing adsorption apparatus 18 is also used here for the hydrogen-containing fresh gas stream 26, which fresh gas stream 26 is obtained from a hydrogen-obtaining arrangement 27. The hydrogen-obtaining arrangement 27 consists of a steam reformer 28 which is supplied with a natural gas stream 31 and from which a synthesis gas stream 32 comprising carbon oxides and hydrogen is obtained. This synthesis gas stream 32, in order to increase its hydrogen content, is fed to a reactor 29 of the hydrogen-obtaining arrangement 27 for the water-gas shift reaction, from which reactor 29 the fresh gas stream 26 is then obtained. The purge gas 19 from the pressure swing adsorption apparatus 18 can then be used together with a fuel gas 30 for operation of the steam reformer 28. In a departure from the working examples of FIGS. 1 to 4, the pressure swing adsorption apparatus 18 and the hydrogen-obtaining arrangement 27 added in this working example are also part of a chemical plant 33, with the pressure swing adsorption apparatus 18 being part of this chemical plant 33 and part of the plant proposed for synthesis of methanol.

By virtue of the common use of the pressure swing adsorption apparatus 18, the return stream 4 from the hydrogen recovery arrangement 8 forms the H stream 3, such that the return stream 4 is thus fed as H stream 3 to the methanol reactor arrangement 7. As shown in FIG. 5, only a portion of the hydrogen obtained from the hydrogen recovery arrangement 8 forms the return stream 4, and the further hydrogen can be fed to a use in the chemical plant 33.

Figure 6:
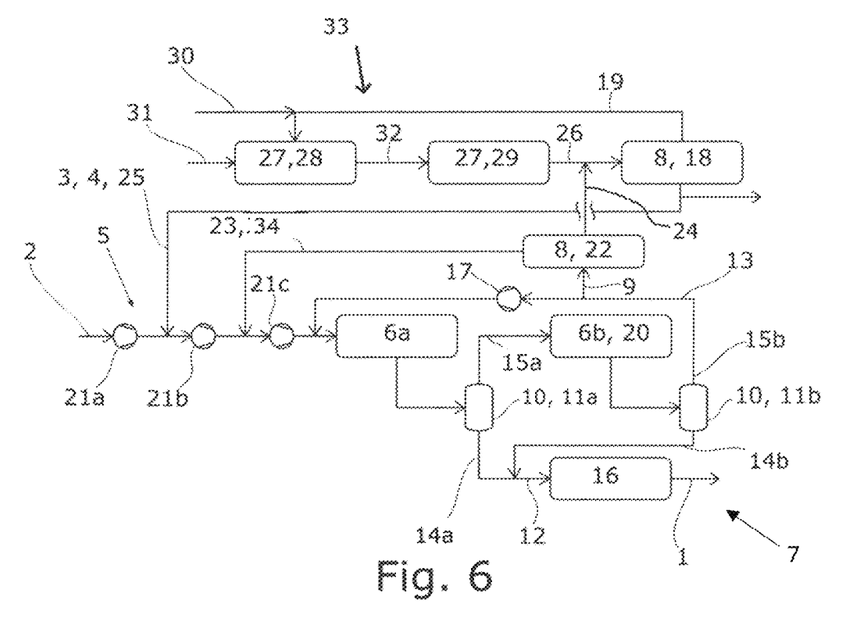
FIG. 6 is a schematic flow diagram of an example plant for executing the process of a sixth working example.

Finally, the plant according to a sixth working example of the plant proposed as shown in FIG. 6 may likewise be operated by the process proposed and proceeds from the fifth working example. However, the hydrogen recovery arrangement 8 here, similarly to the fourth working example, has a membrane apparatus 22 and a pressure swing adsorption apparatus 18. In accordance with the fourth working example, the membrane tail stream 24 here too is fed to the pressure swing adsorption apparatus 18, specifically together with the fresh gas stream 26. The PSA hydrogen stream 25 then forms the return stream 4 which, after its pressure has been increased by the feed gas compressor arrangement 5, is fed as H stream 3 to the methanol reactor arrangement 7. The membrane hydrogen stream 23 forms a further return stream 34 which, after its pressure has been increased by the feed gas compressor arrangement 5, is fed to the methanol reactor arrangement 7.

What is claimed is:
1. A process for synthesizing methanol comprising:
supplying a CO2 stream that includes a molar proportion of at least 50% carbon dioxide and an H stream that includes a molar proportion of at least 50% hydrogen to a methanol reactor arrangement for conversion to methanol;

obtaining a tail gas stream that comprises unreacted hydrogen from the methanol reactor arrangement;

supplying the tail gas stream from the methanol reactor arrangement, together with a hydrogen-containing fresh gas stream from a hydrogen-obtaining arrangement, to a hydrogen recovery arrangement to obtain a return stream that comprises unreacted hydrogen, wherein the return stream includes a molar proportion of at least 50% hydrogen; and returning the return stream or at least the unreacted hydrogen to the methanol reactor arrangement as the H stream.

2. The process of claim 1 wherein the hydrogen recovery arrangement includes a pressure swing adsorption apparatus for obtaining the return stream from the tail gas stream.

3. The process of claim 2 wherein the hydrogen recovery arrangement includes a membrane apparatus for obtaining the return stream from the tail gas stream, wherein the tail gas stream is fed to the membrane apparatus to obtain a membrane hydrogen stream and a membrane tail stream, wherein the membrane tail stream is fed to the pressure swing adsorption apparatus to obtain a pressure swing adsorption hydrogen stream.

4. The process of claim 1 comprising:

returning a recycle stream comprising unreacted tail gas from the methanol reactor arrangement to the methanol reactor arrangement for partial conversion to methanol; and pressurizing the recycle stream by a recycle compressor arrangement before returning the recycle stream to the methanol reactor arrangement.

5. The process of claim 4 comprising feeding the return stream to the recycle stream prior to pressurizing by the recycle compressor arrangement.

6. The process of claim 4 wherein the methanol reactor arrangement comprises a methanol separation arrangement for obtaining the tail gas stream and a crude methanol stream, wherein the recycle stream is obtained from the methanol separation arrangement.

7. The process of claim 6, wherein the methanol reactor arrangement has a multitude of reactor stages for methanol synthesis that are connected in series, and wherein the methanol separation arrangement has a multitude of methanol separation apparatuses, wherein each methanol separation apparatus is connected downstream of a reactor stage of the multitude of reactor stages.

8. The process of claim 7 comprising obtaining a crude methanol substream and a stage tail gas stream comprising unreacted hydrogen from each of the methanol separation apparatuses of the multitude of methanol separation apparatuses, wherein up to a last reactor stage of the multitude of reactor stages, each stage tail gas stream from one of the methanol separation apparatuses is fed to a downstream reactor stage, the process comprising combining the crude methanol substreams to give the crude methanol stream.

9. The process of claim 7 comprising feeding the CO2 stream, the H stream, the return stream, and the pressurized recycle stream to a first reactor stage of the multitude of reactor stages.

10. The process of claim 9 wherein the tail gas stream is obtained from a methanol separation apparatus that is connected downstream of a tail gas recovery reactor stage, wherein the tail gas recovery reactor stage is connected downstream of the first reactor stage, wherein the tail gas recovery reactor stage is last in series among the multitude of reactor stages.

11. The process of claim 1 wherein the CO2 stream, the H stream, and the return stream, before being fed to the methanol reactor arrangement, are pressurized by a feed gas compressor arrangement, wherein the feed gas compressor arrangement has a multitude of compressor stages that are connected in series, wherein the H stream is supplied to the feed gas compressor arrangement for pressurization between different compressor stages of the multitude of compressor stages.

12. The process of claim 1 wherein a majority of the CO2 stream is carbon dioxide and/or a majority of the H stream is hydrogen.

13. A plant for synthesizing methanol, the plant comprising a methanol reactor arrangement configured to be supplied with a CO2 stream that includes a molar proportion of at least 50% carbon dioxide and an H stream that includes a molar proportion of at least 50% hydrogen for conversion to methanol, wherein the methanol reactor arrangement is configured to produce a tail gas stream comprising unreacted hydrogen and configured to receive the unreacted hydrogen in the tail gas stream that is at least partially returned to the methanol reactor arrangement as the H stream, wherein the plant includes a hydrogen recovery arrangement configured to be supplied with the tail gas stream from the methanol reactor arrangement, together with a hydrogen-containing fresh gas stream from a hydrogen-obtaining arrangement, and to produce a return stream comprising the unreacted hydrogen, wherein the return stream includes a molar proportion of at least 50% hydrogen.

14. The process of claim 1 wherein the tail gas stream is combined with the hydrogen-containing fresh gas stream before they are supplied to the hydrogen recovery arrangement to obtain the return stream.

15. The process of claim 1 wherein the tail gas stream is supplied directly from the methanol reactor arrangement to the hydrogen recovery arrangement and the hydrogen-containing fresh gas stream is supplied directly from the hydrogen-obtaining arrangement to the hydrogen recovery arrangement.

16. The process of claim 1 wherein the hydrogen-containing fresh gas stream is supplied directly from the hydrogen-obtaining arrangement to the hydrogen recovery arrangement.

17. The process of claim 16 wherein the hydrogen-obtaining arrangement includes a plant for obtaining hydrogen by electrolysis.

18. The process of claim 16 wherein the hydrogen-obtaining arrangement includes a steam reformer.

* * * * *